United States Patent
Choi et al.

(10) Patent No.: US 8,925,650 B2
(45) Date of Patent: Jan. 6, 2015

(54) SLIDE-TYPE CORE RETAINER FOR SAMPLE COLLECTOR

(75) Inventors: Dong Lim Choi, Gyeongsangnam-do (KR); Sung Rok Cho, Gyeonggi-do (KR); Won Joon Shim, Gyeongsangnam-do (KR); Moon Koo Kim, Gyeongsangnam-do (KR); Kwan Koog Kim, Gyeonggi-do (KR)

(73) Assignee: Korea Ocean Research and Development Institute (KR)

( * ) Notice: Subject to any disclaimer, the term of this patent is extended or adjusted under 35 U.S.C. 154(b) by 14 days.

(21) Appl. No.: 13/266,250

(22) PCT Filed: Jun. 17, 2010

(86) PCT No.: PCT/KR2010/003912
§ 371 (c)(1),
(2), (4) Date: Oct. 26, 2011

(87) PCT Pub. No.: WO2010/147406
PCT Pub. Date: Dec. 23, 2010

(65) Prior Publication Data
US 2012/0073875 A1    Mar. 29, 2012

(30) Foreign Application Priority Data
Jun. 19, 2009    (KR) .................. 10-2009-0055031

(51) Int. Cl.
*E21B 25/10*    (2006.01)
*G01N 1/08*    (2006.01)
*E02D 1/04*    (2006.01)

(52) U.S. Cl.
CPC ... *E02D 1/04* (2013.01); *G01N 1/08* (2013.01)
USPC .......................................... 175/58; 175/245

(58) Field of Classification Search
CPC ....................................................... E21B 25/10
USPC ......... 175/5, 20, 58, 245, 248, 249, 244, 251;
73/864.65, 863, 864, 864.51, 864.63
See application file for complete search history.

(56) References Cited

U.S. PATENT DOCUMENTS 1,773,915 A * 8/1930 Lydon .............................. 175/44
2,140,417 A * 12/1938 Conklin ......................... 175/236

(Continued)

FOREIGN PATENT DOCUMENTS

JP          07116704         5/1995
JP          2004045081       2/2004

(Continued)

OTHER PUBLICATIONS

International Search Report for International Appln. No. PCT/KR2010/003912 mailed Feb. 1, 2011.

*Primary Examiner* — Jennifer H Gay
*Assistant Examiner* — George Gray
(74) *Attorney, Agent, or Firm* — RatnerPrestia

(57) ABSTRACT

A slide-type core retainer for a sample collector including a sampler tube driven into a sea floor. The slide-type core retainer includes a catcher holder detachably coupled to a tip end of the sampler tube; a catcher installed on an inner peripheral surface of a tip end of the catcher holder and configured to allow sediment introduction into the sampler tube and preventing sediment from being lost using resiliency. A control member slidably installed inside the catcher holder controls opening and closing of the catcher. The control member is coupled to the catcher before sample collection so that the catcher remains opened. The control member slides into an inner side of the catcher holder while being separated from the catcher by the resistance of the solid sediment such that the catcher is closed, when resistance is generated by solid sediment after the sampler tube is driven into the sediment.

4 Claims, 5 Drawing Sheets

(56) References Cited

U.S. PATENT DOCUMENTS 3,504,750 A * 4/1970 Rouviere et al. .............. 175/244
3,952,817 A * 4/1976 Anderson ..................... 175/240
6,394,192 B1 * 5/2002 Frazer ............................ 175/58

FOREIGN PATENT DOCUMENTS

KR    100807240 B1    2/2008
KR    100848876 A1    7/2008

* cited by examiner

SLIDE-TYPE CORE RETAINER FOR SAMPLE COLLECTOR

This application is a U.S. National Phase Application of PCT International Application No. PCT/KR2010/003912, filed Jun. 17, 2010.

BACKGROUND OF THE INVENTION

1. Field of the Invention

The present invention relates to a slide-type core retainer for a sample collector, and more particularly to a slide-type core retainer for a sample collector, which is mounted to a sample collector, such as a corer, used for identifying a vertical property of seafloor sediment, thereby making it possible to easily collect samples without dispersing soft surface sediment.

2. Description of the Prior Art

In general, samples have been collected from sedimentary layers in order to obtain various data, such as physiochemical properties and structures of the strata of a river, a lake, or the sea floor.

A representative apparatus capable of collecting samples of the sedimentary layers is a corer, and many other sample collectors have been commercially used. However, the conventional sample collectors have a disadvantage in that sediment is easily lost when collecting samples of the sedimentary layers, etc.

In this respect, a "basket-type core retainer" that overcomes the above disadvantage is disclosed in U.S. Pat. No. 3,952,817.

As illustrated in FIG. 1, the basket-type core retainer has a structure in which when the core retainer is driven into the strata, basket-type finger members 15 and 16 formed at a tip end of a core tube 11 are opened so as to allow sediment to be introduced, and when the core retainer is lifted from the strata, the basket-type finger members 15 and 16 are resiliently closed so as to prevent the introduced sediment from being lost.

However, since the conventional basket-type core retainer has a structure in which the finger members for opening and closing the tip end of the core tube are opened by resistance of the sediment, it disperses the soft surface sediment while collecting samples, so it is impossible to obtain accurate data from the sample collection.

SUMMARY OF THE INVENTION

Accordingly, the present invention has been made to solve the above-mentioned problems occurring in the prior art, and the present invention provides a slide-type core retainer for a sample collector, in which a sample collector is driven into sediment while a tip end of the sample collector is opened and the tip end of the sample collector remains closed when the sample collector collects samples while being driven into sediment so that soft surface sediment cannot be dispersed by the tip end of the sample collector while samples of seafloor sediment are collected.

The technical problem to be solved in the present invention is not limited to the aforementioned technical problem and other non-mentioned technical problems will be clearly understood by those skilled in the art from the following description.

The aforementioned technical problem to be solved in the present invention may be solved by a slide-type core retainer for a sample collector including a sampler tube driven into the seafloor through a driving unit according to an embodiment of the present invention.

In accordance with an aspect of the present invention, there is provided a slide-type core retainer for a sample collector including a sampler tube driven into a sea floor through a driving unit, the slide-type core retainer including; a catcher holder detachably coupled to a tip end of the sampler tube; a catcher installed on an inner peripheral surface of a tip end of the catcher holder and configured to allow sediment to be introduced into the sampler tube and prevent the introduced sediment from being lost using resiliency; and an opening/closing control member slidably installed inside the catcher holder so as to control opening and closing of the catcher, The opening/closing control member is coupled to the catcher before collection of samples to make a control so that the catcher compulsorily remains opened, and when resistance is generated by solid sediment of deep strata after the sampler tube is driven into the sediment, the opening/closing control member slides into an inner side of the catcher holder while being separated from the catcher by the resistance of the solid sediment of deep strata to make a control such that the catcher is closed.

Further, the opening/closing control member has a pipe-like shape whose opposite ends are opened so that it prevents the generation of resistance by soft surface sediment after the sampler tube is driven into the sediment.

Furthermore, the catcher includes a plurality of resilient pieces, and one side of each of the resilient pieces is mounted on the inner peripheral surface of the tip end of the catcher holder and an opposite side of each of the resilient pieces contacts an outer peripheral surface of the opening/closing control member before collection of samples, and it contacts each other at a central portion of the catcher holder when the sampler tube is separated from the opening/closing control member by the resistance of the solid sediment of deep strata after the sampler tube is driven into the sediment.

The slide-type core retainer for the sample collector according to an embodiment of the present invention makes a control such that the tip end of the sampler tube is driven into the sea floor while being opened and remains closed during the collection of samples, so that it can easily collect samples without dispersing soft surface sediment and prevent the sediment from being lost, thereby increasing accuracy of collected samples.

Further, the slide-type core retainer for the sample collector according to the embodiment of the present invention can be formed in accordance with a standard sampler tube and can be easily applied to various corers.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE EXEMPLARY EMBODIMENTS

Hereinafter, an exemplary embodiment of a slide-type core retainer for a sample collector according to the present invention will be described with reference to the accompanying drawings. Further, in the following description of the present invention, a detailed description of known functions and configurations incorporated herein will be omitted when it may make the subject matter of the present invention unclear.

Figure 1:
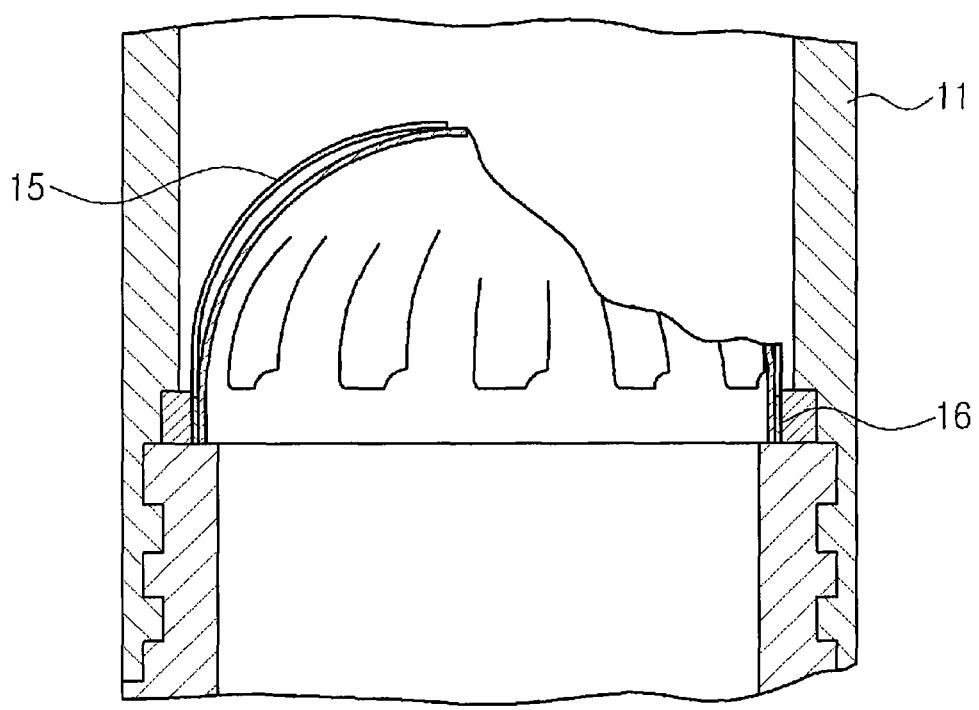
FIG. 1 is a sectional view illustrating a conventional sample collector for seafloor sediment.
Figure 2:
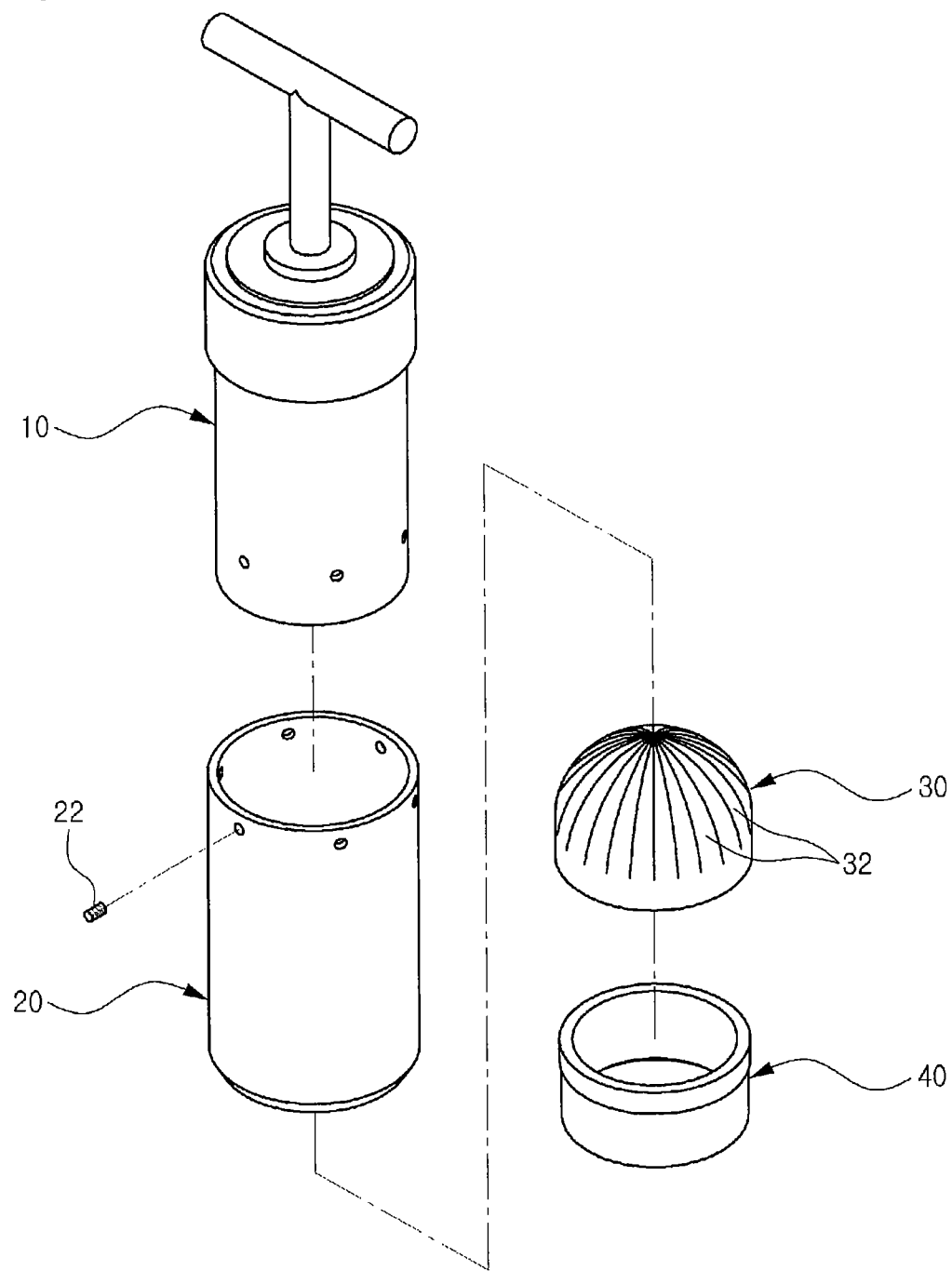
FIG. 2 is a perspective view illustrating a slide-type core retainer for a sample collector according to the present invention.
Figure 3:
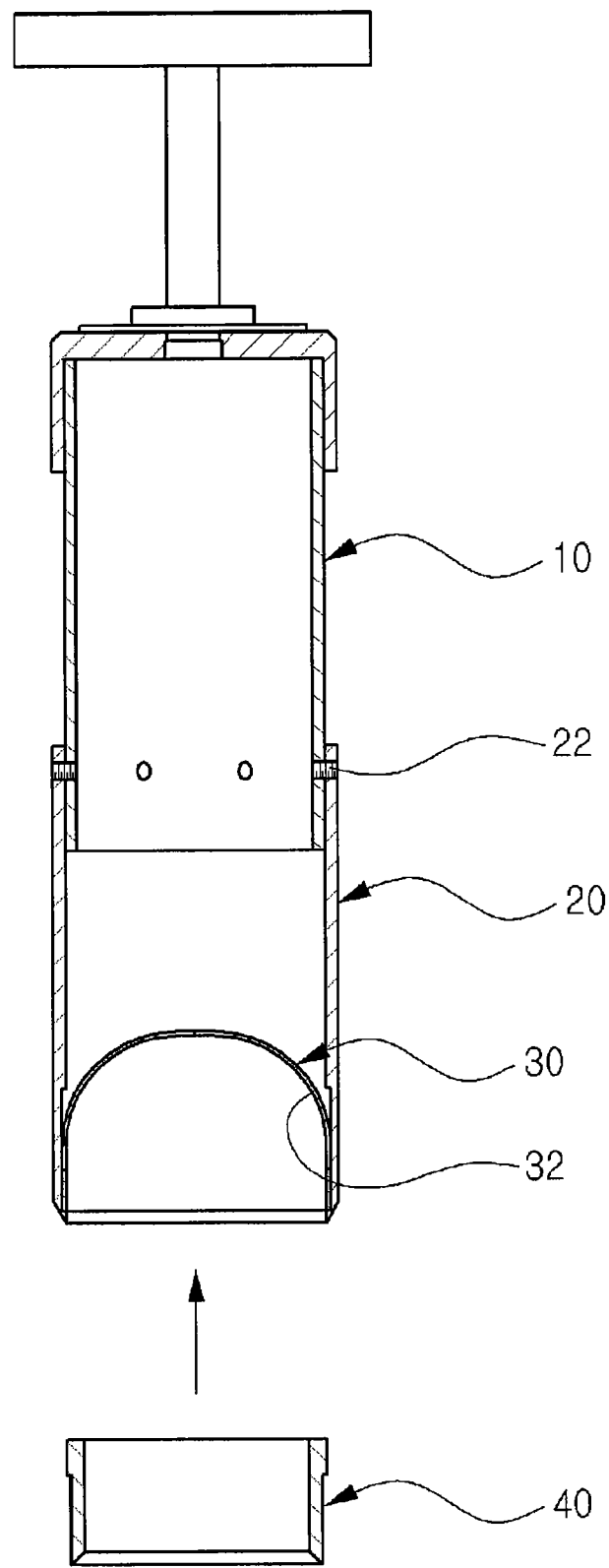
FIG. 3 is a sectional view illustrating the slide-type core retainer for a sample collector of FIG. 2.
Figure 4:
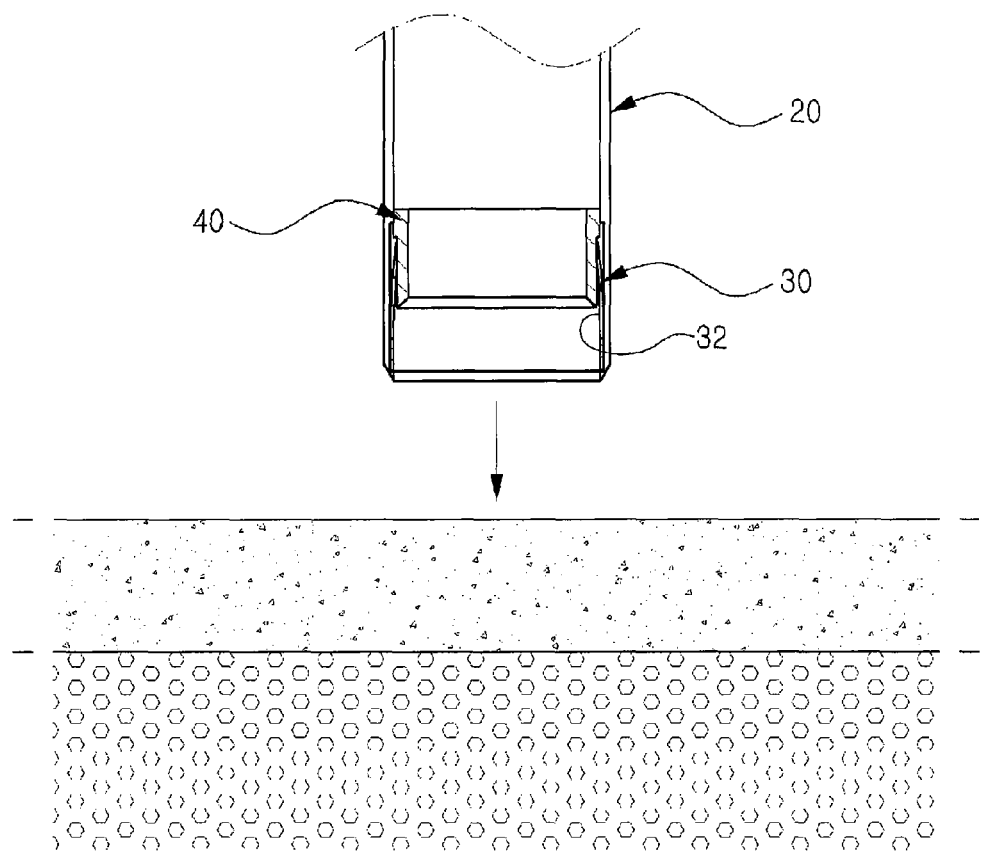
FIG. 4 is a sectional view illustrating a state in which a tip end of the sample collector is opened by the slide-type core retainer according to the present invention.
Figure 5:
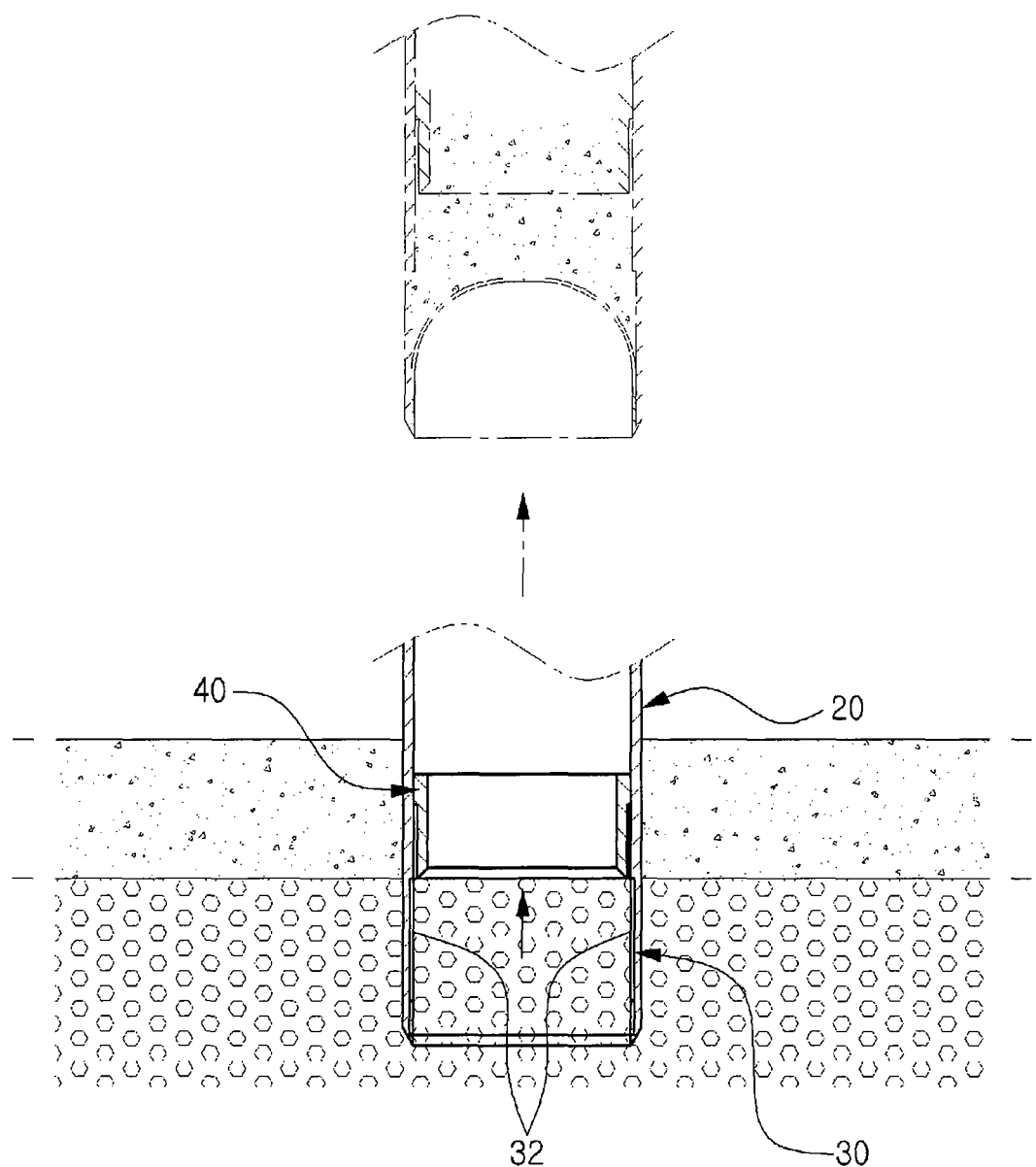
FIG. 5 is a sectional view illustrating a state in which the tip end of the sample collector is closed by an operation of the slide-type core retainer according to the present invention.

FIG. 2 is a perspective view illustrating a slide-type core retainer for a sample collector according to the present invention; FIG. 3 is a sectional view illustrating the slide-type core retainer for a sample collector of FIG. 2; FIG. 4 is a sectional view illustrating a state in which a tip end of the sample collector is opened by the slide-type core retainer according to the present invention; and FIG. 5 is a sectional view illustrating a state in which the tip end of the sample collector is closed by an operation of the slide-type core retainer according to the present invention.

As illustrated in FIGS. 2 and 3, the slide-type core retainer for a sample collector according to the present invention includes a catcher holder 20 coupled to a tip end of a sampler tube 10 driven into the sea floor through a driving unit, a catcher 30 installed in the catcher holder 20 and configured to allow sediment to be introduced into the sampler tube 10 and to prevent the introduced sediment from being lost using resiliency, and an opening/closing control member 40 for controlling opening and closing of the catcher 30.

Specifically, the catcher 20 is hollow and is detachably installed at the tip end of the sampler tube 10 by means of a coupling member 22. In this case, the coupling member 22 is at least one bolt, but may be any conventional coupling means capable of detachably coupling the catcher holder 20 to the sampler tube 10.

The catcher 30 includes a plurality of resilient pieces 32 and contacts an inner peripheral surface of a tip end of the catcher holder 20. The catcher 30 has a basket-like shape convexly protruding toward the sampler tube 10 with the plurality of resilient pieces 32 such that the catcher 30 normally remains closed.

The catcher 30 has a structure by which the catcher 30 is opened so as to allow sediment to be introduced into the sampler tube 10 when the sampler tube 10 is driven into the sea floor and remains closed so as to prevent the sediment introduced into the sampler tube 10 from being lost when the sampler tube 10 is lifted from the sea floor using resiliency of the resilient pieces 32.

The opening/closing control member 40 serves to control the opening and closing of the catcher 30. To this end, the opening/closing control member 40 is substantially ring-shaped and is slidably coupled to an inner side of the catcher holder 20.

That is, the opening/closing control member 40 is coupled to the catcher 30 at an initial stage (before the sampler tube is driven into the sea floor) to make a control so that the catcher 30 is compulsorily opened. Meanwhile, when resistance is generated by solid sediment of deep strata while the sampler tube 10 is driven into the sediment and collects samples, the opening/closing control member 40 is separated from the catcher 30 by the resistance and slides into the inner side of the catcher holder 20 to make a control so that the catcher 30 is closed.

Since the sampler tube 10 driven into the sea floor through the driving unit while collecting samples of the seafloor sediment is driven into the sediment while the tip end of the sampler tube 10 is compulsorily opened by the opening/closing control member 40, it does not disperse soft surface sediment. Further, since the tip end of the sampler tube 10 remains closed by resistance of the solid strata when the sampler tube 10 collects samples while being driven into the sea floor, it is possible to prevent the samples collected in the sampler tube 10 from being lost.

An operation of the present invention having the above construction is described hereinbelow.

As illustrated in FIG. 4, in the slide-type core retainer for a sample collector according to the present invention, the opening/closing control member 40 is coupled to the catcher 30 at an initial stage (before the sampler tube is driven into the sea floor) for collecting samples of sedimentary layers. Then, the resilient pieces 32 are opened when the catcher 30 is coupled to the opening/closing control member 40, so as to compulsorily open the catcher 30. The sampler tube 10 driven into the sea floor through the driving unit is driven into the sedimentary layers while the catcher 30 is opened according to the coupling of the opening/closing control unit 40, so that the sampler tube 10 is driven into the strata without dispersing soft surface sediment.

Accordingly, the sampler tube 10 does not disperse soft surface sediment and prevents the sediment from being damaged, thereby easily collecting samples.

In the meantime, as illustrated in FIG. 5, when the sampler tube 10 driven into the sea floor bumps into relatively solid sediment of deep strata, the opening/closing control member 40 slides into the inner side of the catcher holder 20 while being naturally separated from the catcher 30 due to the resistance of the sediment of deep strata. Then, the catcher 30 is resiliently restored and closed due to the separation of the opening/closing control member 40 when the sampler tube 10 is lifted.

Accordingly, it is possible to prevent the samples introduced into the interior of the sampler tube 10 from being lost when the sampler tube 10 is lifted after samples of the seafloor sediment are completely collected.

Meanwhile, since the sizes of the catcher holder 20, the catcher 30, and the opening/closing control member 40 may be adjusted depending on the standard of the sampler tube 10, they may be applied to various corers.

Although an exemplary embodiment of the present invention has been described for illustrative purposes, those skilled in the art will appreciate that the present invention is not limited to the exemplary embodiment of the present invention and various changes and modifications are possible, without departing from the scope and spirit of the invention as disclosed in the accompanying claims. Therefore, those skilled in the art will appreciate that the changes and modifications are not separated from the technical aspect or spirit of the present invention and modified embodiments belong to scope of the appended claims of the present invention.

What is claimed is:

1. A slide-type core retainer for a sample collector comprising a sampler tube driven into a sea floor through a driving unit, the slide-type core retainer comprising:
   a catcher holder detachably coupled to a tip end of the sampler tube;
   a catcher installed on an inner peripheral surface at a lowermost end surface of the catcher holder, which makes first contact with the sea floor, and is configured to allow sediment to be introduced into the sampler tube and prevent the introduced sediment from being lost using resiliency; and an opening/closing control member slidably installed inside the catcher holder so as to control opening and closing of the catcher, wherein the opening/closing control member is coupled to the catcher before collection of samples so that the catcher compulsorily remains opened while the opening/closing control member is entirely positioned within the inner peripheral surface of the catcher holder so that the lowermost end surface of the catcher holder makes first contact with the sea floor, and the opening/closing control member slides into an inner side of the catcher holder while being separated from the catcher by the resistance of the solid sediment of deep strata to make a control such that the catcher is closed, when resistance is generated by solid sediment of deep strata after the sampler tube is driven into the sediment.

2. The slide-type core retainer as claimed in claim 1, wherein the opening/closing control member has a pipe-like shape whose opposite ends are opened to prevent the generation of resistance by soft surface sediment after the sampler tube is driven into the sediment.

3. The slide-type core retainer as claimed in claim 1, wherein the catcher comprises a plurality of resilient pieces, and one side of each of the resilient pieces is mounted on the inner peripheral surface of the catcher holder and an opposite side of each of the resilient pieces contacts an outer peripheral surface of the opening/closing control member before collection of samples, and each of the resilient pieces contacts each other at a central portion of the catcher holder when the catcher is separated from the opening/closing control member by the resistance of the solid sediment of deep strata after the sampler tube is driven into the sediment.

4. The slide-type core retainer as claimed in claim 2, wherein the catcher comprises a plurality of resilient pieces, and one side of each of the resilient pieces is mounted on the inner peripheral surface of the catcher holder and an opposite side of each of the resilient pieces contacts an outer peripheral surface of the opening/closing control member before collection of samples, and each of the resilient pieces contacts each other at a central portion of the catcher holder when the catcher is separated from the opening/closing control member by the resistance of the solid sediment of deep strata after the sampler tube is driven into the sediment.

* * * * *